(12) United States Patent
Levine et al.

(10) Patent No.: US 6,687,544 B1
(45) Date of Patent: Feb. 3, 2004

(54) SYSTEM AND METHOD FOR DETERMINING SAFETY ALERT CONDITIONS FOR IMPLANTABLE MEDICAL DEVICES

(75) Inventors: Paul A. Levine, Santa Claria, CA (US); Bruce L. Wilkoff, So. Russell, OH (US); Brian M. Mann, Beverly Hills, CA (US); Allan R. Schwartz, Moorpark, CA (US)

(73) Assignee: Pacesetter, Inc., Sylmar, CA (US)

( * ) Notice: Subject to any disclaimer, the term of this patent is extended or adjusted under 35 U.S.C. 154(b) by 235 days.

(21) Appl. No.: 09/970,217

(22) Filed: Oct. 2, 2001

Related U.S. Application Data

(63) Continuation of application No. 09/432,918, filed on Nov. 2, 1999, now Pat. No. 6,327,501.

(51) Int. Cl.[7] .............................. F61N 1/05; F61N 1/37
(52) U.S. Cl. ....................................................... 607/27
(58) Field of Search ................................ 607/27, 28, 29, 607/31, 34, 60, 63, 1; 128/898

(56) References Cited

U.S. PATENT DOCUMENTS

| | | | |
|---|---|---|---|
| 5,199,439 A | 4/1993 | Zimmerman et al. | 128/670 |
| 5,262,944 A | 11/1993 | Weisner et al. | 364/413.02 |
| 5,321,800 A | 6/1994 | Lesser | 395/140 |
| 5,331,549 A | 7/1994 | Crawford, Jr. | 364/413.02 |
| 5,357,427 A | 10/1994 | Langen et al. | 364/413.02 |
| 5,361,202 A | 11/1994 | Doue | 364/413.01 |
| 5,371,692 A | 12/1994 | Draeger et al. | 364/580 |
| 5,416,695 A | 5/1995 | Stutman et al. | 364/413.02 |
| 5,500,854 A | 3/1996 | Uotila | 370/17 |
| 5,507,786 A | 4/1996 | Morgan et al. | 607/27 |
| 5,724,985 A | 3/1998 | Snell et al. | 128/697 |
| 6,327,501 B1 * | 12/2001 | Levine et al. | 607/27 |

* cited by examiner

Primary Examiner—Jeffrey R. Jastrzab (57) ABSTRACT

A system and method for identifying and displaying safety alert advisories. The system of the present invention automatically performs a comparison of identification data with a safety alert advisory. The system stores identification data in a plurality of dedicated fields. Each of the dedicated fields contains information related to the patient. Upon the telemetric retrieval of the data by an external programmer, the external programmer automatically cross-correlates the data in the dedicated fields with the safety alert advisories. Upon identification of a match between the data and one of the safety alert advisories, the identified safety alert advisory is displayed to a medical practitioner. In addition, the system provides a dedicated memory to store an advisory flag. The advisory flag is marked when the programmer identifies a safety alert condition that is relevant to one of the dedicated fields. When a subsequent external programmer retrieves the data from the dedicated fields, the external programmer can notify the medical practitioner that a safety alert advisory exists even though the safety alert advisory was never directly input into the subsequent external programmer.

10 Claims, 5 Drawing Sheets

FIG. 1

| PART | FLAG | TIME |
|---|---|---|
| IMPLANTABLE DEVICE MODEL NUMBER | | |
| IMPLANTABLE DEVICE SERIAL NUMBER | | |
| ATRIAL LEAD MODEL NUMBER | | |
| ATRIAL LEAD SERIAL NUMBER | | |
| VENTRICLE LEAD MODEL NUMBER | | |
| VENTRICLE LEAD SERIAL NUMBER | | |
| PULSE GENERATOR MODEL NUMBER | | |
| PULSE GENERATOR SERIAL NUMBER | | |
| CLOCK MODEL NUMBER | | |
| CLOCK SERIAL NUMBER | | |
| TELEMETRIC CIRCUIT MODEL NUMBER | | |
| TELEMETRIC CIRCUIT SERIAL NUMBER | | |
| BATTERY MODEL NUMBER | | |
| BATTERY SERIAL NUMBER | | |
| PATIENT COMPLICATIONS | | |

SYSTEM AND METHOD FOR DETERMINING SAFETY ALERT CONDITIONS FOR IMPLANTABLE MEDICAL DEVICES

CROSS-REFERENCE TO RELATED APPLICATIONS

This application is a continuation of U.S. patent application Ser. No. 09/432,918, filed Nov. 2, 1999 now U.S. Pat. No. 6,327,501.

FIELD OF THE INVENTION

This invention relates to implantable medical devices, and in particular, to implantable medical devices that are capable of comparing safety alert information to medical data.

BACKGROUND OF THE INVENTION

Some implantable medical devices, such as pacemakers, defibrillators, and cardioverters (collectively referred to as implantable cardiac stimulation devices) are designed to monitor and stimulate the cardiac tissue of patients who suffer from cardiac arrhythmias. Using leads connected to the patient's heart, a cardiac stimulation device typically stimulates cardiac tissue by delivering electrical pulses in response to measured cardiac events which are indicative of a cardiac arrhythmia. Properly administered therapeutic electrical pulses often successfully reestablish or maintain the heart's normal rhythm, commonly referred to as normal sinus rhythm (NSR).

Implantable cardiac stimulation devices can treat a wide range of cardiac arrhythmias by using a series of adjustable parameters to alter the energy content, shape, location, and frequency of the therapeutic pulses. As such, these devices are now in widespread use and have become increasingly sophisticated over time. However, with the increased sophistication of the devices, the possibility of the devices experiencing difficulty following implantation has increased. It is very desirable that medical practitioners who are overseeing patients with implanted devices be kept advised of the problems experienced with other implanted devices so that the medical practitioners can take protective action with their own patients, if necessary. Generally, medical practitioners review device and heart performance data stored in a memory within the implanted device via a telemetry circuit that is part of the implanted device and an external programmer. While this provides the medical practitioner the ability to assess device performance, the practitioner must be able to determine if the implanted device includes components that have had problems in other implanted devices.

If and when a systematic problem is identified in a given model device, the manufacturers will notify the medical community via a letter describing the potential problems identified in a specific model device with recommendations as to patient management with respect to that potential system behavior. These safety alert bulletins advise medical practitioners of a possible problem based on observations from other implanted stimulating devices of the same model. An example of a safety alert information is a warning from a manufacturer indicating that a particular lead is suspect or that a type of pulse generator is prone to a specific unexpected behavior including but not limited to sudden no-output performance.

This type of information may provide an explanation to the medical practitioner for an observed performance characteristic of one of their patient's implanted devices or may even induce the medical practitioner to institute corrective actions even up to performing surgery to replace a suspect device. Moreover, the safety alert information may also provide recommended parameter ranges that the medical practitioner can use to set performance parameters of the implanted device using the programmers.

However, in practice, even if a medical practitioner reads the safety alert information sent by the device manufacturer, the medical practitioner may not recollect receiving the safety alert when examining a patient with an implantable device some months or even years later. In addition, the specific medical practitioner may never have received notification having not been registered as the medical practitioner following a patient with a suspect device when that patient enters the medical practitioner's practice at a later date. As a consequence, the medical practitioner may not always take the necessary corrective action.

Although implantable devices have been developed to perform some self-diagnostics, there currently does not exist a way to automatically cross-correlate safety alert information to medical data which is maintained on the implantable medical device.

In fact, the current generation implanted stimulation devices are not well adapted to even receive the information. For example, the more sophisticated implantable medical devices may include a small general storage memory that a medical practitioner may use to enter and store patient information. However, while a provider of the implantable medical device may recommend various types of information be included in this memory, it is the medical practitioner who ultimately decides what data is to be included in the memory. Typical patient information that is stored in the general storage memory include: a patient name, date of implant, model and serial numbers of atrial and ventricular leads, date of implant of atrial and ventricular leads if different from the pacemaker, diagnoses, and name of a monitoring medical practitioner. However, the medical practitioner may not necessarily store the aforementioned information in any particular order. Therefore, a computerized analysis of the data in an implanted device to assess if the device or devices have been included in a safety alert or other specific warning from the manufacturer is problematic since a computer system does not know the type and memory location of information contained in the general storage memory and whether the information is, in fact, even present.

Hence, while the current generation implantable stimulation devices include memories that are adapted to store information downloaded by a medical practitioner that can be subsequently recalled, the memories are not generally formatted in a manner that will allow for an automatic safety alert assessment. In particular, there are no existing protocols for storing the safety alert data in the device memory. Moreover, the memories are generally not adapted to display safety alert information to medical practitioners who are subsequently reviewing the device performance via an external programmer. Consequently, medical practitioners may not be able to recall all of the safety alert information for a particular implanted device. This may result in the medical practitioner overlooking a particular problem or misinterpreting data and setting device parameters incorrectly.

Therefore, there is a need for an implantable medical device which is capable of correlating safety alert, special warning and advisory information from the manufacturer for the model devices that comprise the implanted system including the electronic device and one or more peripheral components such as the leads. To this end, there is a need for a system which can receive safety alert information and compare this information to information about a patient's implanted cardiac device so that the communicating device or programmer can provide an appropriate warning to an evaluating medical practitioner following interfacing with the implanted device.

SUMMARY OF THE INVENTION

The present invention relates to implantable medical devices, and in particular to implantable medical devices that are capable of comparing safety alert information to medical data stored within the implantable medical device.

The aforementioned needs are satisfied by the implantable medical device system of the present invention which includes an implanted medical device that is adapted to provide therapy to the patient and has a memory and a telemetry circuit capable of providing data stored in the memory to an external programmer. The memory of the implanted device is adapted to include identification data which can include either component identification data (e.g., data identifying the pulse generator and associated leads) or patient complication identification data or both, in an accessible location within the memory. The system also includes an external programmer that has a telemetry circuit capable of interrogating the implanted medical device and retrieving the identification data. The external programmer also includes a memory that has safety alert data contained therein. The external programmer is capable of being periodically updated with information provided by the manufacturer as to safety alerts and other warnings that may have only been recognized and generated some time after the original system implantation. The external programmer is adapted to retrieve the identification data from the memory of the implanted device and then compare this identification data to the safety alert information to determine if any of the safety alert information is relevant to the implanted system. If the information is relevant, the external programmer is adapted to provide a signal to the medical practitioner of the existence of the safety alert and can be further adapted to provide additional information and recommendations about the safety alert information to the medical practitioner.

In one embodiment, both the identification data and the safety alert data include device identifiers that identify the components of the implanted system and the specific devices affected by the safety alert information. The external programmer is adapted to search the implanted component identifiers provided by the implanted device to determine if any of the identifiers are the subject of a safety alert. The safety alert information can consist of potentially defective components or complications experienced by this particular patient. The external programmer can then automatically provide a signal to the medical practitioner of the existence of a potential problem while the medical practitioner is actually treating or evaluating the patient. In one embodiment, the safety alert information in the external programmer can be periodically updated by computer disk, network (e.g., Internet) access or using any of a number of well-known procedures for updating computer memories.

In this way, the system of the present invention is capable of providing real time warnings to the medical practitioner of the existence of a problem at a time when the medical practitioner is reviewing device and patient performance parameters. It is therefore less likely that the medical practitioner will overlook a particular safety alert or other special notification issues that affects the implanted medical device.

These and other objects and advantages will become more fully apparent from the following description taken in conjunction with the accompanying drawings.

DETAILED DESCRIPTION OF THE INVENTION

The following detailed description is directed to certain specific embodiments of the invention. However, the invention can be embodied in a multitude of different ways as defined and covered by the claims. In this description, reference is made to the drawings wherein like parts are designated with like numerals throughout.

The present invention relates to implantable medical devices, and in particular to implantable medical devices that are capable of comparing safety alert information to medical data stored within the implantable medical device.
System Overview Implantable cardiac stimulation devices are commonly used examples of implantable medical devices and will be used to illustrate the principles of the present invention. It should be understood, however, that the principles of the present invention apply equally as well to any and all other types of implantable medical devices and medical devices in general which have the capability to actively communicate with an external device such as a programmer.

Figure 1:
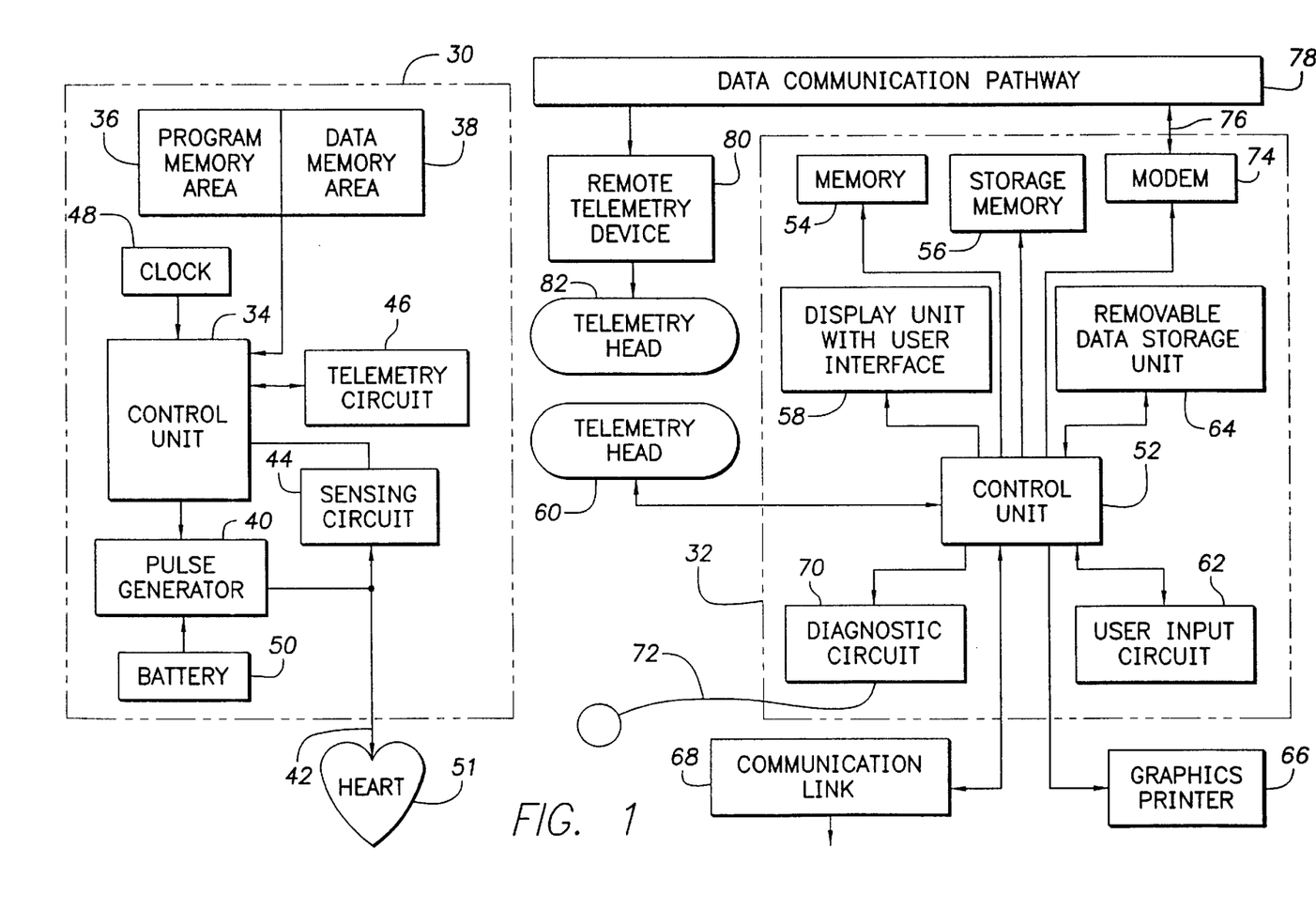
FIG. 1 is a schematic block diagram of an external programmer and implantable medical device of the invention.

An implantable medical device 30 and an external programmer 32 in accordance with this invention are shown in FIG. 1. The implantable medical device 30 may be a pacemaker, a cardioverter/defibrillator (ICD), a combination of both, or any other implantable medical device capable of delivering therapy and being interrogated by an external programmer to noninvasively adjust its functional parameters. For simplification during the discussion of this invention, reference will be made to pacemakers but this should be taken to include all medical devices (e.g., drug pumps, neurostimulators and the like) with these broad capabilities, not just those restricted to the heart. The operation of the implantable medical device 30 is controlled by a control unit 34, which preferably contains control circuitry (not shown) and a microprocessor (not shown) for executing a control program (not shown) that is stored in a program memory area 36.

A data memory area 38 is provided for storing medical data. The program memory area 36 and the data memory area 38 may be memory blocks of a single memory unit (shown as a combination of program memory area 36 and the data memory area 38) or may be two separate memory circuits.

The control unit 34 also includes self-diagnostic circuitry (not shown) for monitoring the operational characteristics of the implantable medical device 30. Such operational characteristics include, but are not limited to, battery voltage, battery current, internal battery impedance, and lead impedance. The operational characteristics may be monitored by the implantable medical device 30 between visits. An example of how data pertaining to certain operational characteristics may be acquired between visits is disclosed in the commonly assigned U.S. Pat. No. 5,507,786, issued Apr. 16, 1996, of Mann and Morgan, entitled "System and Method for Measuring and Storing Parametric Data Pertaining to Operating Characteristics of an Implantable Medical Device," which is hereby incorporated by reference in its entirety.

A pulse generator 40 is connected to a patient's heart 51 with at least one lead 42. The lead 42 is used for cardiac data acquisition (e.g., sensing the patient's intracardiac electrogram, or IEGM), as well as for delivery of therapeutic pulses. The at least one lead 42 may, for example, comprise a ventricular lead which stimulates the heart's ventricle, or an atrial lead which can stimulate the heart's atrium or some combination thereof. Therapeutic pulses may be pacing pulses delivered to maintain a normal heart rate, or higher energy shocks delivered to interrupt an occurrence of a tachycardia or fibrillation. The pulse generator 40 generates therapeutic pulses administered through the lead 42 to the patient's heart 51 under direction from the control unit 34. A sensing circuit 44 converts analog data acquired by the lead 42 into a digital form which is capable of being analyzed by the control unit 34. The data is stored in the data memory area 38 and transmitted to the external programmer 32 by telemetry through an internal telemetry circuit 46. A clock 48 is used to provide timing for monitoring cardiac events and for timing the application of therapeutic pulses by the pulse generator 40. A battery 50 supplies the necessary power to the pulse generator 40 (and to other components of the implantable medical device 30, as necessary, through connections that are not shown).

The implantable medical device 30 is similar in configuration and operation to any of a number of implantable medical devices of the prior art. The implantable medical device 30 is capable of sensing when the heart is in need of a therapeutic stimulation and then providing the therapeutic stimulation. The implantable medical device 30 is also capable of assessing the success of the therapeutic stimulation and adjusting the delivery of further therapy accordingly. The implantable medical device 30 is also capable of recording various device and patient parameters in memory 38 for subsequent review by a medical practitioner via the telemetry circuit 46 and the external programmer 32 in a manner that is known in the art. With these types of devices, medical practitioners generally periodically review the performance of the device with follow up visits with the patient following implantation of the implantable medical device 30.

In an exemplary embodiment, the external programmer 32 is a pen-based tablet computer such as the one disclosed in the above-incorporated U.S. Pat. No. 5,724,985. One such external programmer 32 is an APS III Model 3500 Programmer available from St. Jude Medical CRMD, of Sylmar, Calif. Of course, other types of programmers may be used.

The external programmer 32 is controlled by and connected to a control unit 52, which is preferably microprocessor-based. A programmer memory 54 (preferably random access memory) is used by the control unit 52 for software operation and data processing, while a storage memory 56 is used for long-term data storage. The storage memory 56 may be any type of memory suitable for long-term data storage including a hard disk drive, flash memory, or a rewritable optical disk.

Figure 2A:
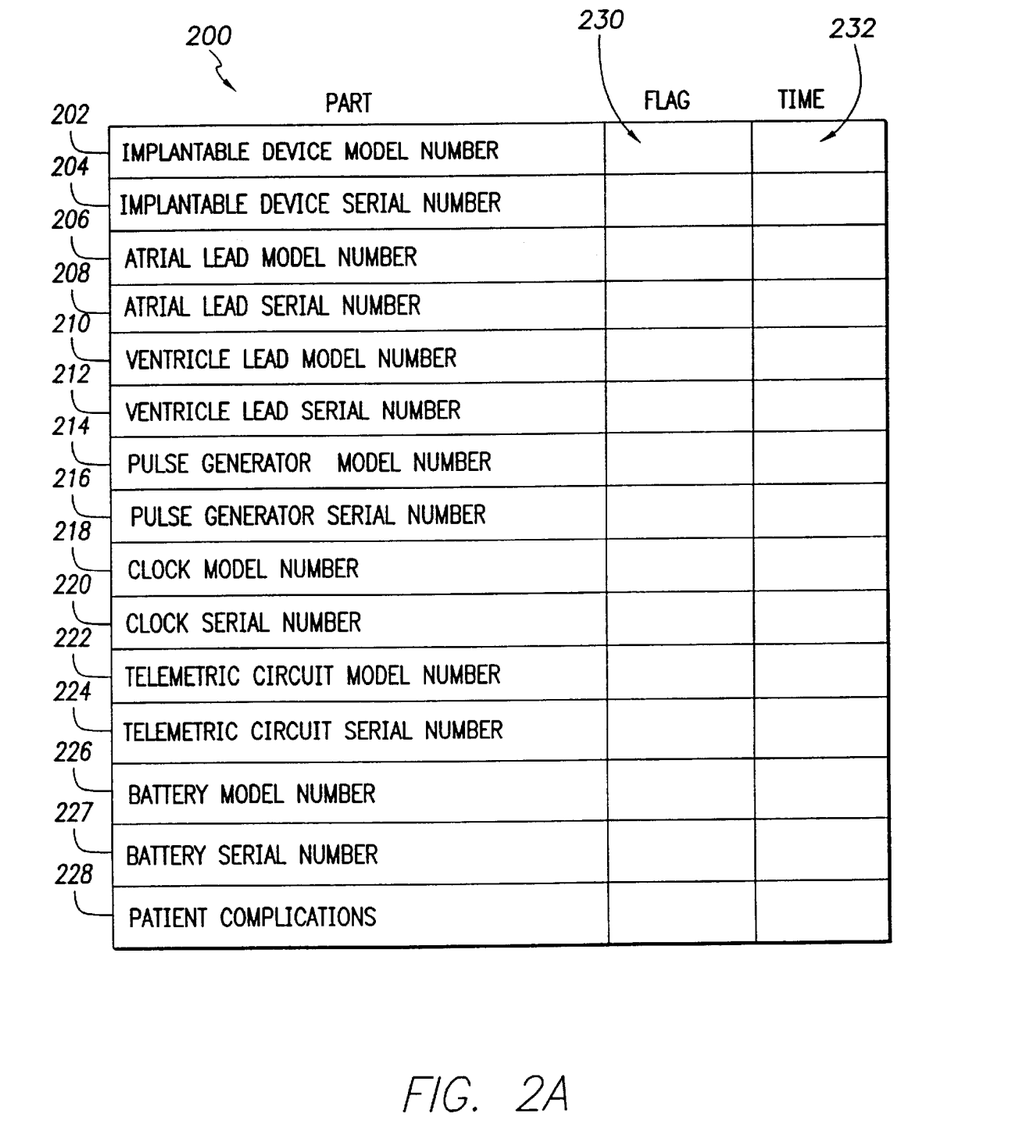
FIG. 2A is a diagram illustrating an exemplary data structure incorporating a plurality of dedicated fields which are stored in a memory in the implantable medical device of FIG. 1.
Figure 2B:
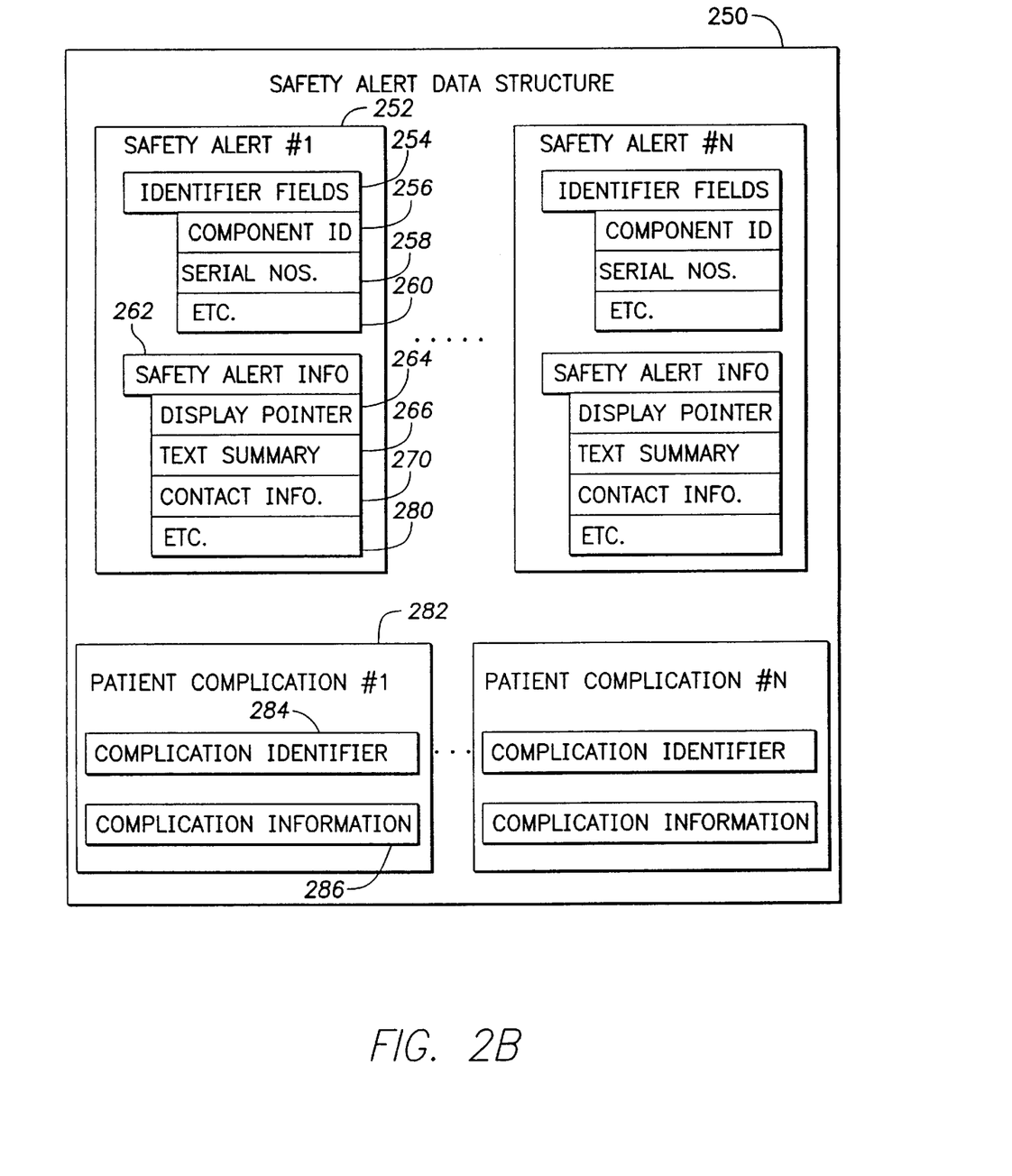
FIG. 2B is a diagram illustrating an exemplary data structure incorporating the safety alert information that is stored in the memory of the external programmer.

In this embodiment, the storage memory 56 is also adapted to store safety alert information (FIG. 2B). As will be discussed in greater detail below, the safety alert information that is stored in the memory 56 is provided via disk or tape (i.e., a transportable media) or a communication link (e.g., the Internet, a LAN, or the like), in a format enabling it to be periodically updated and selected to allow for automatic comparison of the safety alert data in its memory to the specific device characteristics or components of the implantable medical device 30 by the external programmer 32. The safety alert data in the memory 56 may, for example, include: warning advisories from medical manufacturers, research information from educational groups, or advisory information created by a treating medical practitioner. Optionally, the safety alert information may be stored for convenience in a computer database (not shown) that is accessible by the external programmer 32 during follow-up review of the implantable medical device 30.

The external programmer 32 is also preferably provided with a graphical display unit 58. The display unit 58 is used to display recently acquired medical data obtained from the implantable medical device 30. An external telemetry head 60 is used to communicate with the implantable medical device 30 through conventional telemetry.

The medical practitioner interacts with the external programmer 32 through a user input device 62, which may be a keyboard, a pen, or even a voice interface. A removable data storage unit 64, such as a floppy disk drive, is also provided for exporting data from the storage memory 56 or the programmer memory 54. One type of data that may be exported is the historical medical data file which the medical practitioner may want to give to a traveling patient or save as a backup copy, in case the original file becomes corrupted.

An external printer 66 may be used to print graphical or textual data at the medical practitioner's request. An optional communication link 68 may be used to connect to a separate computer system, such as a hospital mainframe (not shown), a network, e.g., the Internet (not shown), or a dedicated PC database computer (not shown) for transferring data to and from the external programmer 32. The communication link 68 may be a physical connection or a remote connection such as an infrared, a radio frequency, or a cellular link. A diagnostic circuit 70, connected to the control unit 52, converts analog data acquired by a plurality of external leads 72 into digital form. The digital data may be analyzed by the control unit 52 and stored in the programmer memory 54. A power source for the external programmer 32 may be an on-board battery (not shown) or a power cord (not shown) connected to an electrical power outlet (not shown).

As an alternative to conventional telemetry, a modem 74 enables the external programmer 32 to communicate telemetrically with the implantable device 30 through a data communication pathway 78 (which may be a typical public telephone line, an infrared link, or a cellular link) and a remote telemetry device 80. A data communication link 76 is used to connect the modem 74 to the data communication pathway 78. The data communication link 76 may be a physical connection, a magnetic link or an RF link, e.g., using a cellular antenna. The remote telemetry device 80 is equipped with a telemetry head 82 for communicating with the implantable medical device 30 through telemetry.

Medical information from the implantable medical device 30 can be provided to a medical practitioner using an external programmer 32, such as the one disclosed in the commonly assigned U.S. Pat. No. 5,724,985, issued May 10, 1998, of Snell and Levin, entitled "User Interface for an Implantable Medical Device Using an Integrated Digitizer Display Screen," which is hereby incorporated by reference in its entirety.

The acquisition, processing, display, and storage of medical data are controlled by the external programmer 32 through a control program (not shown). The control program (not shown) may be written in a high-level programming language, e.g., C, C++, BASIC, Pascal, or FORTRAN, and run under a well-known operating system, e.g., MSDOS, Windows, Unix or the like. C, C++, BASIC, Pascal, and FORTRAN are industry standard programming languages for which many commercial compilers can be used to create executable code. The operation of the control program (not shown) is described below in greater detail in reference to FIGS. 3 and 4.

As will be discussed below in greater detail, the external programmer 32 is adapted to periodically receive safety alert information and store this information in the memory 56 or some other memory readily accessible to the external programmer 32. When a medical practitioner uses the external programmer 32 to inspect and analyze the implantable medical device 30, the external programmer 32 then queries the implantable medical device 30 to obtain operational parameters about the implantable medical device 30 or the patient. The external programmer 32 then compares the operation parameters obtained via telemetry from the implantable medical device 30 to the safety alert data stored in the memory 56 to assess whether any of the safety alert information pertains to the particular implantable medical device 30. If the external programmer 32 determines that the safety alert information does pertain to the particular implantable medical device 30, the external programmer 32 then provides a suitable indication to the medical practitioner via the display unit 58. Further, the external programmer 32 may also be adapted to store a suitable indicator in the memory of the implantable medical device 30 so that subsequent medical practitioners may be provided with an indicator indicating that the implantable medical device 30 may include components that are in need of greater scrutiny. The exact operation of the external programmer 32 and the implantable medical device 30 during these processes will now be described in reference to FIGS. 2–4.

The memory 38 of the implantable medical device 30 is adapted to have a data structure 200 for identifying the components which comprise the implantable medical device 30, e.g., the pulse generator and associated leads, etc. An exemplary implementation of the data structure 200 is shown in the table of FIG. 2A. Manufacturers do not routinely inform medical practitioners about specific component problems, e.g., a battery or a telemetry circuit, since individual components cannot typically be replaced. However, the exemplary data structure 200 shown in FIG. 2A enables tracking of components that could, in combination, pose a problem or devices which include suspect components within a specific range of serial numbers. Preferably, the information in the data structure 200 specifically corresponding to the implantable medical device 30, e.g., a pacemaker, is loaded by the manufacturer prior to implantation and information corresponding to the other portions of the implantable medical system, e.g., the leads, are loaded by the medical practitioner during or closely following implantation. The manufacturer specific information with respect to individual components is preferably hidden from the medical practitioner during routine device interrogation but triggers a recommendation to the medical practitioner when a manufacturer safety alert identifies components (as determined by the data within the data structure 200) within a particular implantable medical device 30.

As illustrated, the data structure 200 includes identification information that identifies the various components of the implantable medical device 30, specific components of the entire system such as the pulse generator and lead(s) and also possible complications experienced by the patient. In this embodiment, the data structure 200 is shown as including dedicated element fields for the Implantable Device Model Number 202, the Implantable Device Serial Number 204, the Atrial Lead Model Number 206, the Atrial Lead Serial Number 208, the Ventricle Lead Model Number 210, the Ventricle Lead Serial Number 212, the Pulse Generator Model Number 214, the Pulse Generator Serial Number 216, the Clock Model Number 218, the Clock Serial Number 220, the Telemetric Circuit Model Number 222, the Telemetric Circuit Serial Number 224, the Battery Model Number 226, and the Battery Serial Number 227, but the possible number of options is relatively unlimited and can be altered by redefining the data structure 200.

The fields 202–227 are representative of the specific components that are included in the implantable medical device 30 or the complete implantable medical system which additionally includes the associated leads or other components. The data structure 200 is adapted to include dedicated fields that contain unique identifiers for each of the components of the implantable medical system. As will be discussed in greater detail below, the data structure 200 can be searched by the external programmer 32 to determine if safety alert data, sorted by corresponding component identifiers, apply to the components of the implantable medical system.

As is also shown in FIG. 2A, the data structure 200 also includes a field 228 for identifiers of particular patient complications. In this embodiment, the medical practitioner can download particular codes into the data structure 200 which will provide an indication of particular patient complications, e.g., various heart diseases, lack of tolerance to particular treatment, etc. Accordingly, when a subsequent medical practitioner uses the external programmer 32 to ascertain the status of the patient, these patient complication or special clinical information identifiers can be recognized by the external programmer 32 and the external programmer 32 can then display a pre-selected message to the medical practitioner about the existence of the patient complication or special circumstances.

It will be appreciated that sometimes patients may experience a heart difficulty which results in the patients traveling to the nearest medical facility, particularly when the heart difficulty is an emergency. The medical practitioner who then sees the patient may not be the patient's normal medical practitioner. Thus, storing patient information and complications in the memory 38 of the implantable medical device 30 and providing a corresponding data structure in the external programmer 32 enables the new medical practitioner to be advised of the particular complications and special circumstances at the time the new medical practitioner is investigating the performance of the implantable medical A flag 230 is associated with each of the dedicated fields 202–228 of the data structure 200. The flag 230 is set by the external programmer 32, in a manner that will be described in greater detail below, when safety alert data is found to correspond to the particular component identifier or patient complication found within the dedicated field 202–228. Also, a time stamp 232 is also preferably associated with each of the dedicated fields 202–228 so that an indication of the time that a particular component was flagged as having an associated safety alert can be recorded in the memory 38.

Although the data structure 200 is illustrated as being contained in one contiguous memory, each of the dedicated fields may be optionally stored in discontinuous memory locations. Further, it is to be appreciated that additional dedicated fields may be created for other types of medical data. These fields may include such data as the patient identification information. Hence, the data structure 200 is simply illustrative of one possible list of identifiers that can be used in conjunction with the external programmer 32 and one possible organization of data.

FIG. 2B is a graphical illustration of an exemplary safety alert data structure 250 that is stored in the storage memory 56 of the programmer 32. As illustrated, the data structure 250 includes sub-data structures 252 for each of the safety alerts (1-N) that have been provided to the external programmer 32. The safety alert sub-data structures 252 are organized, in this embodiment, to include identifier fields 254 which may include data lines for the component identification number 252, the component serial number 258 or other identification information 260 that will allow the control unit 52 to determine what components are the subject of the safety alert. The identifier fields 254 of each of the sub-data structures 252 are selected so that the identifier fields will correspond to the identifier fields 202-227 of the data structure 200 stored within the memory 38 of the implantable medical device 30 when the safety alert concerns a component of the implantable medical device 30.

Each safety alert sub-data structure 252 also includes safety alert information fields 262 which can include display pointers 264, text summary information 266, contact information 270 or other additional information that is to be provided to the medical practitioner. In this embodiment, the safety alert information fields 262 include the information that is to be provided to the medical practitioner when the control unit 52 of the external programmer 32 determines that the implantable medical device 30 includes a component that is the subject of a safety alert. The display pointer field 264 may include a prompt to display the information on the display unit 58 along with how the information is to be displayed, e.g., in color, flashing, etc. The text summary 266 may be a textual summary that is to be displayed on the display 58 describing the safety alert so that the medical practitioner can be made aware of the particular safety alert that affects the patient. There may also be telephone numbers, persons or organizations to contact in the contact information field 270 that will allow the medical practitioner to obtain additional information about the safety alert affecting the patient.

As is also shown in FIG. 2B, the data structure 250 also includes patient complication sub-data structures 282 that contain identifiers 284 and information about particular patient complications. In one embodiment, an identifier is stored in the field 228 of the data structure 200 contained within the memory 38 of the implantable medical device 30 may correspond to a sub-data structure 282 that is contained within the memory 56 of the external programmer 32. When the control unit 52 of the external programmer 32 determines that the patient has a particular complication, the information 286 contained in the complication sub-data structure 282 can then be provided to the medical practitioner via the display 58.

Storing the information about the complication in the memory 56 of the external programmer 32 conserves limited memory space within the memory of the implantable device 30. However, the complication information that is stored in each of the external programmers 32 is likely to be a standard list of complications that may not cover particular complications experienced by individual patients. In other embodiments, the information about particular complication can actually be stored in the memory 38 of the implantable medical device 30.

As discussed above, the exact organization of the safety alert data structure 250 will vary depending upon the application. Hence, the diagram of FIG. 2B is illustrative of the type of information that is to be stored in the storage memory 56 about various safety alerts. Moreover, as discussed above, safety alert information will periodically be provided to the each of the external programmers 32 that correspond to a particular series of implantable medical devices 30 in a number of possible manners. Update disks, updates via modem or updates via the Internet or other network interface can be used to periodically update the safety alert data structure 250. Alternatively, written safety alerts can be provided to medical practitioners who can then use this information to update their external programmers 32 via the user input device 62.

Hence, the implantable medical devices 30 are designed to include a data structure that includes fields having identifiers that uniquely identify either the components of the implantable medical device 30 or complications experienced by the patient or both. Preferably, each of the external programmers 32 that are adapted to communicate with the implantable medical devices 30 also include data structures that uniquely identify either components of implantable medical devices 30 that are the subject of safety alerts, particular patient complications or both. The data structures contained within the external programmers 32 also provide additional information about the particular safety alert to the medical practitioner. As will be described in greater detail below, the control unit 52 of the external programmer 32 is adapted to search the data structure 200 in the implantable device 30 and preferably compare both the component identifiers and the complication identifiers contained therein to the component and complication identifiers for the safety alert or patient complication data contained in the structures 252, 282 within the memory 56 of the external programmers 32.

Method of Operation

Figure 3:
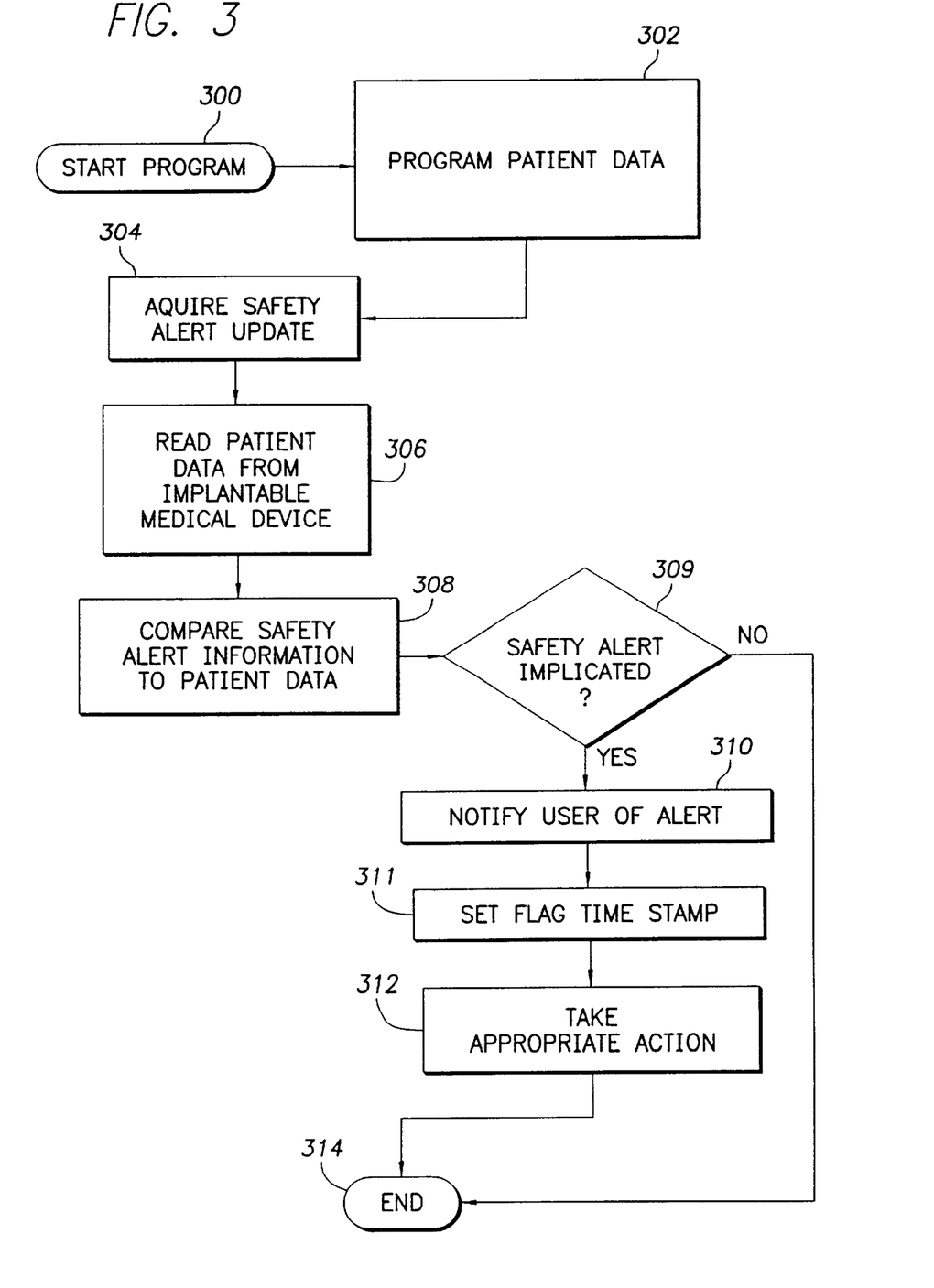
FIG. 3 is a flowchart illustrating a safety alert notification process of the external programmer and implantable medical device of FIG. 1.

Referring now to FIG. 3, a flowchart illustrating a safety alert notification process for the external programmer 32 and the implantable medical device 30 is described below. Before starting at step 300, a medical practitioner has implanted the implantable medical device 30 into a patient in a well-known manner and has initiated the operation of the implantable medical device 30 in a well-known manner. The portion of the control program (not shown) of the external programmer 32 and the implantable medical device 30 relating to the safety alert function is initiated in step 300.

Next, at step 302, the external programmer 32 inputs the medical data into the implantable medical device 30. Optionally, the medical data may be input to the implantable medical device 30 before it is implanted into the patient. In one embodiment, the medical practitioner interacts with the external programmer 32 and the implantable medical device 30 via a graphical user interface 58 of the external programmer 32. The medical practitioner may also use a keyboard (not shown) to enter the identification data into the dedicated fields 202–228.

As discussed above, the implantable medical device 30 stores a variety of parameters in the memories 36 and 38. These parameters include such things as the operational parameters of the implantable medical device 30 and also the identification data stored in the dedicated data fields 202–228 as discussed above. In general, at implantation, the implanting medical practitioner generally sets or directs the setting of the operational parameters of the implantable medical device 30 or the operational parameters may be set to some default values. For example, these operational parameters can, for a pacemaker, include the base rate, the AV delay, the amplitude and width of the pulse to be provided and the sensitivity settings, etc. These operational parameters may be altered subsequent to implantation by a treating medical practitioner using the external programmer 32 in a well-known manner to optimize the performance of the implantable medical device 30 to regulate the patient's heart.

Moreover, as discussed above, the implantable medical device 30 also stores in memory the component and complication data defined by the dedicated data fields 202–228. The component data in this embodiment can either be recorded in the memory 38 at implantation or following implantation.

Next, at step 304, the external programmer 32 acquires safety alert information. It is to be appreciated that the external programmer 32 which acquires the safety alert information need not be the same external programmer 32 which initially programmed the implantable medical device 30. The safety alert information can be communicated to the external programmer 32 by a variety of methods, a few of which are described below.

In one embodiment of the invention, a manufacturer may send a computer diskette containing the safety alert advisory to all of the known medical practitioners who have external programmers 32. The medical practitioner inserts the computer diskette into a disk drive on the external programmer 32, and the control program (not shown) reads in the safety alert information and stores updated safety alert data in the memory 54. In another embodiment of the invention, the external programmer 32 periodically retrieves safety alert data from one or more predefined or other web sites on the Internet, a local network or the like. This safety alert data is then used to update the safety alert data structure in the memory 56. In yet another embodiment of the invention, the medical practitioner inputs the safety alert data via the user input device 62 into the memory storage 56 of the external programmer 32 after receipt of a written safety alert bulletin from the manufacturer.

Moving to step 306, the external programmer 32 retrieves the identification data from the implantable medical device 30 and stores the data in the memory 54 (FIG. 1) for analysis. Continuing to step 308, the external programmer 32 (FIG. 1) compares the safety alert data to the identification data. The external programmer 32 determines if any of the safety alert information is relevant to the patient's condition and/or the patient's implantable medical device 30. In one embodiment of the invention, the external programmer 32 automatically performs a cross-correlation of the safety alert data and the identification data each time the external programmer 32 communicates with the implantable medical device 30. The process for comparing the safety alert data and the identification data is described in greater detail with reference to FIG. 4.

The external programmer 32 then determines, in decision state 309, whether any of the safety alert data contained in the safety alert data structure 250 stored in the memory 58 of the external programmer 32 corresponds to components or complications identified in the data structure 200 stored in the memory 38 of the implantable medical device 30. If the external programmer 32 determines that a safety alert data structure corresponds to a component or complication identified in the data structure 200, the external programmer 32 notifies the medical practitioner, in step 310, of any safety alert information contained in the safety alert data structure about the particular identified component or complication. The external programmer 32 can then display information to the medical practitioner via the display unit 58 indicative of the safety alert information. As discussed above, this information is provided from the information fields 262, 286 in each of the sub-data structures 252, 282 and can, for example, include a brief description of the problem and possibly other information such as a predefined telephone number of an individual or group that can be contacted by the medical practitioner to obtain additional information on the safety alert information.

The external programmer 32 in this embodiment also sends signals to the implantable medical device 30, in state 311, to set the flag 230 and the time stamp 232 corresponding to the particular dedicated field 202–228 contained within the data structure 200. The flag 230 and the time stamp 232 can then provide an indication to a subsequent inquiry by the external programmer 32 that a particular safety alert corresponds to a component of the implantable medical device or a complication experienced by the patient and the time when the safety alert was identified. If the time stamp 232 is implemented, a subsequent external programmer 32 can, by reviewing the time stamp, ascertain whether there has been an update to the safety alert data structure corresponding to the particular safety alert that has not yet been provided to a medical practitioner about this particular patient.

In one embodiment, the external programmer 32 is adapted to review all of the flags 230 that have been previously set in the memory 36 of the implantable medical device 30. In some circumstances, it is possible that the external programmer 32 may not have the relevant safety alert data. In which case, the external programmer 32 can be adapted to display a generic message, e.g., "Safety alert previously recognized for this component, information not in database." Such a message would instruct the medical practitioner to take further action to investigate the nature of the safety alert.

Next, at step 312, the medical practitioner takes appropriate action depending on the context of the safety alert information, if any. The exact steps taken by the medical practitioner depend upon the information about the component or complication that is provided by the external programmer 32 via the display 58. The information can include such things as limitations on device settings or even recommendations for immediate replacement of various components of the implantable medical device 30 which may require invasive surgical procedures.

Figure 4:
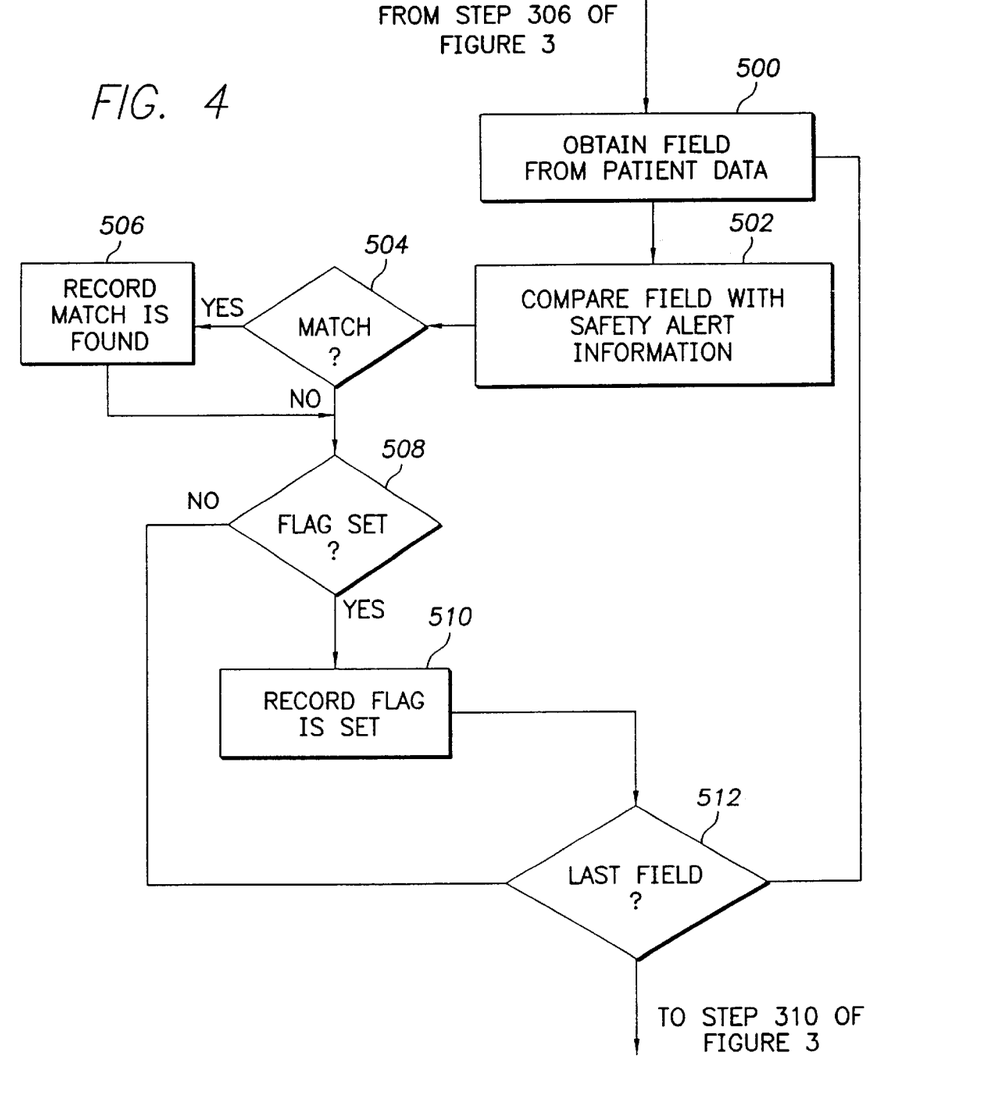
FIG. 4 is a flowchart illustrating a safety alert information identification process, explaining in further detail the steps that occur in the flowchart of FIG. 3.

FIG. 4 is a flowchart illustrating a process for comparing safety alert data in the safety alert data structure 250 stored in the memory 56 of the external programmer 32 with identification data which is within the dedicated fields 202–228 of the data structure 200 contained in the memory 38 of the implantable medical device 30. FIG. 4 shows in greater detail the actions that occur in step 308 of FIG. 3. Before starting at step 500, the external programmer 32 of FIG. 1 has read in all of the identification data identifying device components and patient complications from the data structure 200 contained in the memory 38 of the implantable medical device 30. At step 500, the external programmer 32 obtains the identification data from the first dedicated field. For example, in the embodiment of the invention illustrated with reference to FIGS. 2A–2B, the external programmer 32 retrieves the model number of the implantable medical device 30 provided in dedicated field 202. An exemplary model number for an implantable medical device is "Trilogy DR+ Model 2364."

Next, at step 502, the external programmer 32 compares the identifier data of the current dedicated field with all of the identifier fields 254, 284 of the safety alert data structure 250 (FIG. 2B). In one embodiment of the invention, the external programmer 32 searches the contents of safety alert information for the identifier data in the selected dedicated field. Using the same foregoing example, if the external programmer 32 is analyzing the first dedicated field 202, the external programmer 32 searches the safety alert data structure 250 for the string "Trilogy DR+ Model 2364" in each of the identifier fields of the sub-data structures 252, 282. Alternatively, in another embodiment of the invention, the safety alert data is organized and stored in a database and the external programmer 32 searches for a related safety alert information by performing a database query. In yet another embodiment of the invention, the external programmer 32 searches all of the text of the safety alert information for the text string in selected field.

Moving to step 504, the external programmer 32 determines whether a match between the identifier in the selected dedicated field and an identifier of a safety alert sub-data structure 252 or patient complication sub-data structure 282 has occurred. If the external programmer 32 finds a match, the external programmer 32 proceeds to step 506 and records that a match is found in the memory 54 (FIG. 1). Otherwise, if the external programmer 32 does not find a match, the external programmer 32 proceeds to step 508.

From either step 504 or step 506, the external programmer 32 proceeds to step 508. In step 508, the external programmer 32 determines if the flag 230 for the selected dedicated field is set to determine whether a previous medical practitioner identified relevant safety alert information. Flag 230 of a dedicated field is set if a prior medical practitioner encountered a relevant safety alert information. As discussed above, the flag 230 may be a dedicated space in the dedicated field, or, alternatively, the flag 230 may be a special symbol embedded in the dedicated field. Optionally, if the dedicated fields 202–228 include time stamps, a date of modification of the flag 230 may be compared with the date of any identified safety alert information. If the date of the modification of the flag 230 is later than the date of the safety alert information stored in the memory 54, the external programmer 32 assumes that the current safety alert information is out of date. Conversely, if no safety alert information was found and a flag 230 is marked, the external programmer 32 knows that the external programmer 32 does not have all of the latest safety alert information.

Proceeding to step 510, if a flag 230 is set and the external programmer 32 does not have the latest safety alert information, the external programmer 32 records the safety alert flag 230 in the memory 54 for future reporting in state 310 (FIG. 3). Continuing to decision step 512, the programmer 52 determines whether it has analyzed all of the dedicated fields 202–208. If the external programmer 32 has identified all of the dedicated fields, the external programmer 32 proceeds to step 310 of FIG. 3 to notify the user of the safety alert information. Otherwise, if the current dedicated field is not the last dedicated field, the external programmer 32 returns to step 500 to obtain the medical data from the next dedicated field. The external programmer 32 analyzes, in turn, each of the dedicated fields 202–228 until all of the fields 202–230 have been analyzed. The process then continues to the state 310 of FIG. 3 to notify the user of any safety alert information or safety alert flags that have been identified.

The automatic safety alert check of the present invention overcomes several limitations currently found in the field of medical device implants such as the inability to automatically cross-correlate medical data with safety alert information. The external programmer 32 of the invention provides for the automatic analysis of medical data which is stored in a plurality of dedicated fields 202–208 in the memory of the implantable medical device 30. After the external programmer 32 finds a match between an element of the medical data and the safety alert information, the external programmer 32 notifies the medical practitioner of the safety alert information. Such notification may be a message which is generated on the display 58 or by a computer generated printout. By providing an automatic cross check of the safety alert information with the medical data, the external programmer 32 insures that the medical practitioner is aware of the safety alert information even if the medical practitioner has forgotten that the medical alert is related to the patient's condition, the patient recently entered that medical practitioner's practice, of if the medical practitioner never received notification of the safety alert or other warning from the manufacturer.

Furthermore, the external programmer 32 allows the medical practitioner to flag one of the dedicated fields 202–208 in the event that a safety alert is applicable for the component or condition which is stored in the dedicated field. Optionally, a time stamp 232 may be used to indicate the date that the flag is set. This feature advantageously allows a medical practitioner to notify a subsequent medical practitioner that patient has a condition which the subsequent medical practitioner should be aware of when treating the patient.

Thus, a system and method for identifying and displaying safety alert information are provided. While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. For example, while the cross-correlation of the safety alert data has been described as occurring at the external programmer after device data has been transferred from the implantable medical device to the external programmer, the converse is also considered to be within the scope of the present invention. That is, alternative embodiments include implementations where the cross-correlation occurs at the implantable medical device after the safety alert data has been transferred to the implantable medical device. Accordingly, the scope of the invention is indicated by the appended claims rather than by the foregoing description. All changes which come within the meaning and range of equivalency of the claims are to be embraced within their scope.

What is claimed is:

1. A diagnostic method for use with an implantable medical device system having one or more components, the method comprising:

storing one or more identifiers in a data structure within the implantable medical device system, the identifiers comprising data identifying at least one of the one or more components in the implantable medical device system;

storing safety alert information in a memory within an external programmer;

transmitting one of the identifier data and the safety alert information between the implantable medical device system and the external programmer;

comparing the identifier data with the received safety alert information to determine if one or more identifiers are related to the safety alert information; and notifying a user of relevant safety alert information upon determining that one or more of the identifiers is related to the safety alert information.

2. The method of claim 1, wherein storing one or more identifiers comprises storing a plurality of identifiers in the data structure, the identifiers identifying a plurality of components in the implantable medical device system.

3. The method of claim 1, further comprising modifying the identifiers in the database in the implantable medical device system to indicate the detection of safety alert information for the component corresponding to the identifier.

4. The method of claim 1, wherein receiving safety alert information comprises receiving safety alert information from a network.

5. The method of claim 1, wherein receiving safety alert information comprises receiving safety alert information from the Internet.

6. The method of claim 1, wherein receiving safety alert information comprises receiving safety alert information from a transportable media device.

7. The method of claim 1, wherein comparing the identifiers with the received safety alert information comprises comparing the identifiers from the implantable medical device system to the safety alert information to identify components of the implantable medical device system that are identified in the safety alert information as posing safety risks to patients.

8. The method of claim 1, wherein notifying a user of relevant safety alert information comprises displaying information about the relevant safety alert on a display at the external programmer to the user.

9. The method of claim 1, wherein transmitting one of the identifier data and the safety alert information comprises transmitting the identifier data from the implantable medical device system to the external programmer.

10. The method of claim 1, wherein transmitting one of the identifier data and the safety alert information comprises transmitting the safety alert information from the external programmer to the implantable medical device system.

* * * * *